(12) United States Patent
Lee

(10) Patent No.: US 9,354,178 B2
(45) Date of Patent: May 31, 2016

(54) TRANSMISSION RAMAN SAMPLE ANALYSIS

(71) Applicant: Smiths Detection Inc., Edgewood, MD (US)

(72) Inventor: Vincent Yuan-Hsiang Lee, Winchester, MA (US)

(73) Assignee: Smiths Detection Inc., Edgewood, MD (US)

( * ) Notice: Subject to any disclaimer, the term of this patent is extended or adjusted under 35 U.S.C. 154(b) by 6 days.

(21) Appl. No.: 14/198,056

(22) Filed: Mar. 5, 2014

(65) Prior Publication Data

US 2014/0252234 A1  Sep. 11, 2014

Related U.S. Application Data

(60) Provisional application No. 61/772,703, filed on Mar. 5, 2013.

(51) Int. Cl.
*G01J 5/02* (2006.01)
*G01N 21/65* (2006.01)

(52) U.S. Cl.
CPC ..................................... *G01N 21/65* (2013.01)

(58) Field of Classification Search
CPC ....... G01N 21/65; G01N 21/31; G01N 21/47; G01N 21/55; G01N 2201/06113; G01N 33/487; G01N 35/1065; G01N 21/51; G01N 33/22; G01N 33/566; G01N 35/02; G01J 3/44
USPC ...................................................... 250/341.1
See application file for complete search history.

(56) References Cited

U.S. PATENT DOCUMENTS

| | | | | |
|---|---|---|---|---|
| 4,714,345 A † | 12/1987 | Schrader | | |
| 5,450,193 A * | 9/1995 | Carlsen | ...................... | G01J 3/44 356/246 |
| 5,459,313 A * | 10/1995 | Schrader | ............ | G01N 21/9018 209/524 |
| 5,521,703 A * | 5/1996 | Mitchell | ................ | G01N 21/65 356/301 |
| 7,840,360 B1 * | 11/2010 | Micheels | .................. | G01J 3/42 250/223 B |
| 8,010,301 B2 * | 8/2011 | Hlavaty | .............. | G01N 21/3581 250/341.8 |
| 8,935,960 B2 * | 1/2015 | Wynn | .......................... | 250/338.3 |
| 9,008,408 B2 * | 4/2015 | Sinbar | ................ | G01N 21/3554 382/141 |
| 2002/0154315 A1 * | 10/2002 | Myrick | ..................... | G01J 3/18 356/305 |
| 2004/0063214 A1 * | 4/2004 | Berlin | .................... | G01N 21/65 436/94 |
| 2005/0127285 A1 * | 6/2005 | Kampf | ................. | G01N 33/442 250/281 |
| 2005/0245818 A1 * | 11/2005 | Cyrulnik | ................ | A61B 6/482 600/425 |
| 2007/0138392 A1 * | 6/2007 | Cole | ....................... | G01N 21/49 250/341.1 |

(Continued)

OTHER PUBLICATIONS

Demers: "Multichannel diffuse optical Raman tomography for bone characterization in vivo: a phantom study", Biomedical Optics Express 2012, vol. 3, No. 9, pp. 2299-2305.†

(Continued)

*Primary Examiner* — David J Makiya
*Assistant Examiner* — Taeho Jo
(74) *Attorney, Agent, or Firm* — Advent, LLP

(57) ABSTRACT

Systems and methods for analyzing samples in containers are provided, where an emitter emits radiation at a first location on the container, with a portion of the radiation passing through the container and into the sample, some of the radiation is reflected within the container, a detector receives a transmission Raman signal including Raman radiation from multiple portions of the sample, and a comparator compares the transmission Raman signal with the radiation emitted by the emitter.

32 Claims, 3 Drawing Sheets

(56) References Cited

U.S. PATENT DOCUMENTS

| | | | |
|---|---|---|---|
| 2009/0248322 A1* | 10/2009 | Hlavaty | G01N 21/3563 |
| | | | 702/28 |
| 2010/0053606 A1* | 3/2010 | Matousek | G01N 21/65 |
| | | | 356/301 |
| 2010/0108910 A1 | 5/2010 | Morrell et al. | |
| 2011/0186738 A1 | 8/2011 | Itozaki | |
| 2012/0019834 A1* | 1/2012 | Bornhop | G01N 21/45 |
| | | | 356/517 |
| 2012/0133933 A1* | 5/2012 | Zou | G01N 21/0303 |
| | | | 356/301 |
| 2012/0147370 A1 | 6/2012 | Jiang et al. | |
| 2012/0225475 A1* | 9/2012 | Wagner | G01N 15/14 |
| | | | 435/288.7 |
| 2012/0260998 A1 | 10/2012 | Rodgers | |

OTHER PUBLICATIONS

Zandbergen: "Chemical probing within catalyst bodies by diagonal offset Raman spectroscopy", Angew. Chem. Int. Ed. 2012, 51, 957-960.†

Eliasson_2: "Noninvasive detection of concealed liquid explosives using Raman spectroscopy", published on line at http://pubs.acs.org at time of publication of Eliasson_1—see final paragraph of Eliasson_1 "Supporting information available".†

Eliasson_1: "Noninvasive detection of concealed liquid explosives using Raman spectroscopy", Anal. Chem.2007, 79,8185-8189.†

Olds: "Spatially offset Raman spectroscopy (SORS) for the analysis and detection of packaged pharmaceuticals and concealed drugs", Forensic Science International, 212(1), pp. 69-77.†

\* cited by examiner
† cited by third party

TRANSMISSION RAMAN SAMPLE ANALYSIS

BACKGROUND

The present disclosure relates to spectroscopy, and more particularly to transmission Raman spectroscopy. There are many situations in which a sample is presented, the contents of which are unknown. It may not be immediately obvious what substances are contained in the sample. For example, one may not be able to tell what substances the sample contains by simply looking at the sample, or the like, especially if the sample is within a container. Moreover, it may not be immediately obvious if the sample contains impurities, illicit and/or dangerous substances, substances of interest, or the like.

SUMMARY

Systems and methods are provided for transmission Raman spectroscopy analysis of samples in containers. In one exemplary embodiment, a system configured to analyze a sample in a container is provided, where the system includes an emitter. The emitter is configured to emit radiation directed at a first location on the container. At least a portion of the radiation passes through the container and into the sample. At least a portion of the radiation in the sample is reflected within the container. The system includes a detector with a receiving portion directed at a second location on the container. The detector is configured to receive a transmission Raman signal including Raman radiation from multiple portions of the sample. The system includes a comparator. The comparator is configured to compare the transmission Raman signal with the radiation emitted by the emitter.

Another exemplary embodiment system is provided wherein the first location is an angular distance of between approximately 1° and approximately 179° from the second location. Yet another exemplary embodiment system is provided wherein the first location is an angular distance of one of approximately 135°, approximately 45°, and approximately 90° from the second location. Still another exemplary embodiment system is provided wherein the first location is not located an angular distance of approximately 180° from the second location. Another exemplary embodiment system is provided wherein the system is configured to analyze samples within both generally opaque containers and generally transparent containers.

Yet another exemplary embodiment system is provided, further comprising a sensor configured to determine when a container is configured relative to the system such that a sample within the container may be analyzed by the system. Still another exemplary embodiment system is provided, wherein the sensor is a pressure or other sensor configured to sense the presence of a container. Another exemplary embodiment system is provided, further comprising a second detector directed at a third location on the container located approximately 180° from the first or second locations, the second detector configured to receive a signal including Raman radiation indicative of the material of the container. Yet another exemplary embodiment system is provided, further comprising a processor configured to indicate the presence of predetermined substances within the sample based on the output of the comparator.

Yet another exemplary embodiment system is provided, wherein the angular distance between the entry point through a wall of the container of the emission path and the entry point through a wall of the container of the detection path is greater than zero degrees and less than 180 degrees.

An exemplary embodiment method is provided for transmission Raman analysis comprising: emitting LASER radiation towards a first wall portion of a container, wherein the emitted radiation becomes a diffusive light source within the container without formation of a distinct sample region; receiving a transmission Raman signal from a second wall portion of the container, the received signal including Raman radiation reflected from multiple portions of the container; and comparing the transmission Raman signal with the emitted radiation.

Yet another exemplary embodiment is provided wherein the Raman signal is received through a collection path that is not focused on any distinct sample region within the container. Still another exemplary embodiment is provided wherein no reference beam is used, the method further comprising: receiving a Raman signal including container background information; looking up matching container background information; and subtracting the looked-up container background information from the received Raman signal. Another exemplary embodiment is provided wherein the matching container background information is selected from a table comprising entries for a plurality of glass types and a plurality of plastic types. Yet another exemplary embodiment is provided wherein the emitted LASER radiation follows an incident non-reflected path that intersects a collection path of the Raman radiation corresponding to the received Raman signal.

Yet another exemplary embodiment method is provided, wherein said wall is disposed on at least one of a side or bottom of the container, without an air gap between the wall and the container's contents. Still another exemplary embodiment system is provided, wherein said container is inverted with its cap at the bottom and an air gap at the top. Another exemplary embodiment method is provided, wherein the emitted radiation includes at least one of focused or non-focused light.

Yet another exemplary embodiment method is provided, wherein the emitted radiation illuminates the entire contents of the container by the internal reflection of radiation between the inner walls of the container. Still another exemplary embodiment method is provided, wherein a Raman signal is generated from multi-path LASER excitation of a whole liquid sample within the container. Another exemplary embodiment method is provided, wherein Raman signal is at least one of omni-directional or ubiquitous.

Yet another exemplary embodiment method is provided, wherein the container is opaque Another exemplary embodiment method is provided, wherein said first wall portion is defined by an outer surface of the container, and said second wall portion is defined by an inner surface of the container directly interior to said outer surface.

An exemplary embodiment method of analyzing a sample in a container having an interior surface and an exterior surface is provided. The method includes directing a beam of radiation at the container such that at least a portion of the radiation passes through the container and is scattered in the sample and at least a portion of the scattered radiation reflects off of the interior surface of the container, the radiation in the sample resulting in emission of a Raman signal representative of the contents of the sample at a plurality of locations within the sample. The method includes detecting the Raman signal representative of the contents of the sample at plurality of locations within the sample. The method includes comparing the Raman signal to the radiation of the radiation source.

Another exemplary embodiment method is provided, wherein the directing comprises at least one of: directing a beam of radiation at an opaque container and detecting the Raman signal representative of the contents of a sample contained in the opaque container; or directing a beam of radiation at a non-opaque container and detecting the Raman signal representative of the contents of a sample contained in the non-opaque container. Yet another exemplary embodiment method is provided, wherein the radiation source is a laser of between approximately 50 mW and 500 mW. Still another exemplary embodiment method is provided, wherein the sample comprises a liquid sample. Another exemplary embodiment method is provided, wherein the radiation source is configured to emit a beam of radiation sufficient that a sample contained in a generally opaque container will emit a transmission Raman signal sufficient for the detecting. Yet another exemplary embodiment method is provided, wherein the radiation in the sample is reflected in the container; and wherein the radiation travels in the sample resulting in emission of Raman radiation at various angular orientations with respect to the sample.

An exemplary embodiment method of analyzing liquid samples in both generally opaque containers and generally transparent containers, respectively, is provided. The method includes directing a beam of radiation at a first location on a container containing a liquid sample. The method includes directing a detector at a second location on the container, the second location being different from the first location. The beam of radiation and the detector are configured so a sufficient amount of radiation from the beam passes through the container and into the sample to produce a sufficient transmission Raman signal including Raman radiation from a plurality of locations in the sample so that the detector can detect the transmission Raman signal, the transmission Raman signal being indicative of the composition of the sample. The method includes comparing the transmission Raman signal with the radiation emitted by the emitter. The method includes determining based on a library of characteristics of substances of interest whether the transmission Raman signal indicates that the sample contains a substance of interest. The method includes outputting whether or not the sample contains a substance of interest.

Yet another exemplary embodiment method is provided, wherein an intensity of the transmission Raman signal is angularly independent if the beam of radiation is directed at a generally opaque container. Still another exemplary embodiment method is provided, further comprising determining whether the transmission Raman signal indicates that the sample contains at least one of acetone, cyclohexane, ethanol, ethylene glycol, or H2O2 and outputting a warning if it is determined that the transmission Raman signal indicates that the sample contains at least one of acetone, cyclohexane, ethanol, ethylene glycol, or H2O2. Another exemplary embodiment method is provided, wherein the first location is approximately 135° from the second location. Yet another exemplary embodiment method is provided, further comprising before directing the beam of radiation at the first location on the container, detecting whether a container is located to receive the beam of radiation.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number may identify the figure in which the reference number first appears. The use of the same reference number in different instances in the description and the figures may indicate similar or identical items.

DETAILED DESCRIPTION

Before turning to the Figures, determining the contents of samples may be useful in many situations. For example, it may be useful to prevent samples containing illicit and/or dangerous substances from being transported, such as by airplane passengers carrying samples of fluids, solids, or the like, that need to be checked to determine whether the samples contain any illicit, dangerous, or other substances of interest or if the samples should be discarded before the passenger is allowed through security. In another example, it may be useful to analyze samples to determine whether the samples contain impurities, such as samples flowing through containers such as conduits, samples stored in containers such as packaging, or the like. In many scenarios, however, analysis of samples is further complicated by the fact that the samples are located in containers, such as in the cases of airplane passengers carrying fluid samples in bottles, for example, or where factories may have samples of interest flowing through piping, or where medicine makers may store medicine samples in containers, or the like. Some users may want to analyze a sample without having to remove the sample from its container, such as by non-invasive sample analysis, regardless of whether the container is substantially transparent, translucent, or substantially opaque.

Figure 1:
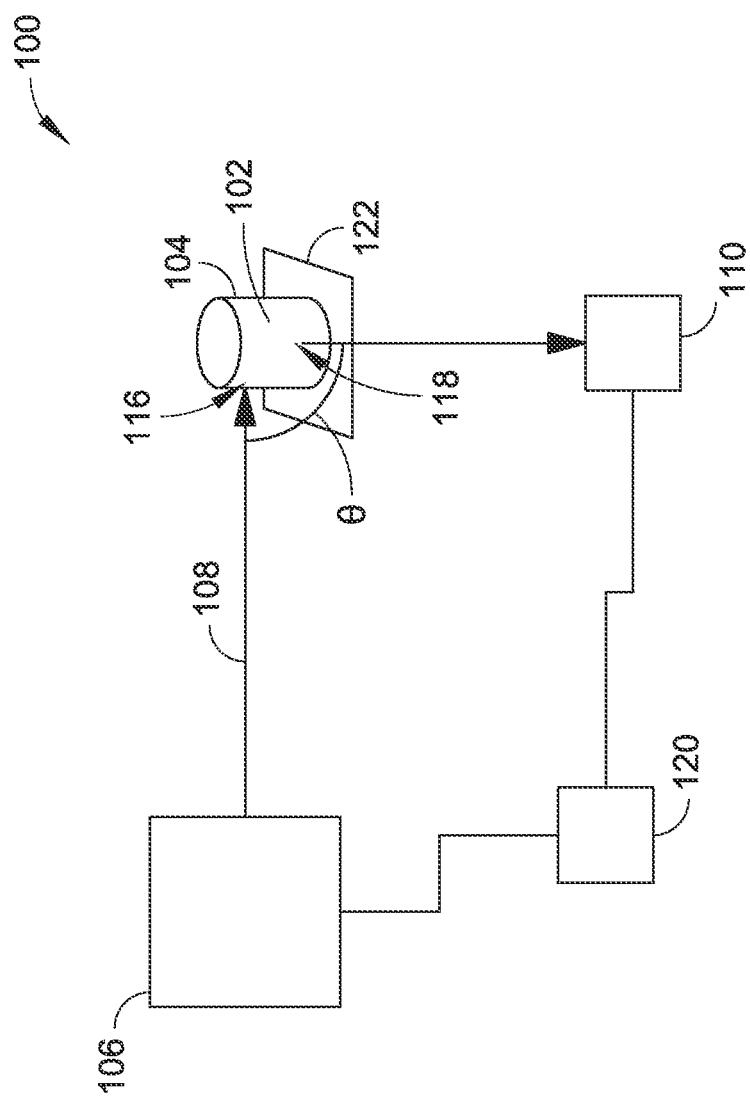
FIG. 1 is a schematic illustration of an exemplary system embodiment configured to analyze a sample contained in a container, without opening of the container or removal of the sample from the container, based on a transmission Raman signal.

With reference to FIG. 1, a schematic representation of an exemplary embodiment transmission Raman sample analysis system is indicated generally by the reference numeral 100. The system 100 is configured to analyze a sample 102 contained in a container 104 without removing the sample 102 from the container 104 or opening the container 104 using non-invasive analysis. The system 100 includes an energy source, such as a radiation source, shown in FIG. 1 as a laser 106. In multiple exemplary embodiments, the laser 106 is a diode laser. In one such embodiment, the laser 106 emits radiation with a wavelength of between approximately 10 nanometers (nm) and approximately 1.1 micrometers. In another embodiment, the laser 106 emits radiation with a wavelength of between approximately 785 nm and approximately 920 nm. In another embodiment, the laser 106 emits radiation with a wavelength of approximately 785 nm. In other embodiments, other suitable radiation sources may be used.

The laser 106 is configured to direct a beam of radiation 108 at the container 104. The system 100 also includes a detector, illustrated in FIG. 1 as a charge-coupled device (CCD) detector 110. In other embodiments, other suitable detectors, such as, for example, single channel detectors, vacuum phototubes, photomultiplier tubes, semiconductor devices, photodiodes, avalanche photodiodes, array detectors, CCD image detectors, infrared array detectors, or the like may be used. The detector 110 is configured to be directed toward the container 104.

Samples to be analyzed may be provided in various types of containers, such as, for example, glass containers, plastic containers, plastic containers including high density polyethylene (HDPE) and/or polyethylene terephthalate (PET), paper containers, clear containers, generally transparent containers, translucent containers, generally opaque containers, tinted containers, or the like. It may be useful to analyze samples regardless of which of these types of containers contains the sample.

In some systems configured to detect Raman radiation, laser light is focused on a location on a container and a detector is focused on the same location on the container. The signal detected by a detector is collected back-scattered (e.g., collected from reflected energy, reflected generally around 180°, etc.) from the sample illumination zone. This back-scattered signal may tend to be indicative of the material of the container itself, especially if the container is generally opaque. That is, the Raman signal emitted might only be indicative of the surface layer, and in the case of a container containing a sample, might only be indicative of the material from which the container is formed, and might not be sufficiently indicative of the material of the sample contained in the container, such as in exemplary cases of containers with low transmission efficiency where low amounts of energy may pass through the container, low amounts of energy may be emitted from the container, and higher amounts of background energy from the container itself may be present.

With further reference to FIG. 1, in embodiments of the system 100, the beam of radiation 108 emitted by the laser 106 is configured such that a portion of the radiation from the laser 106 passes through a wall of the container 104 and into the sample, regardless of whether the container is generally transparent, translucent, or generally opaque.

Figure 2:
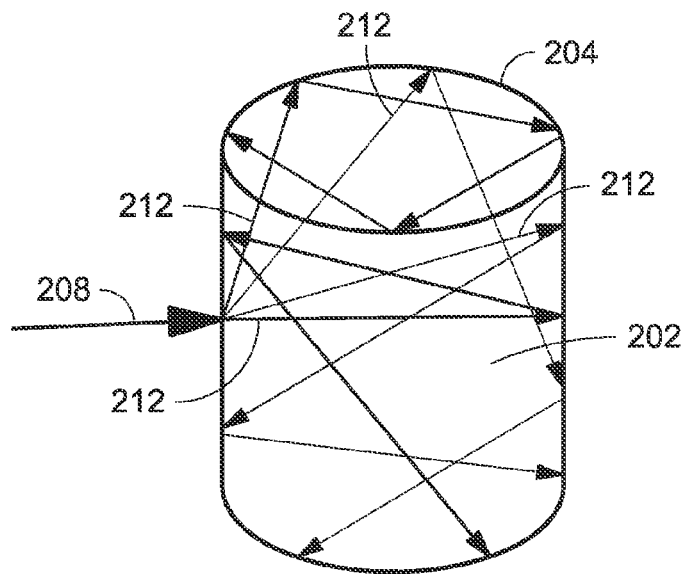
FIG. 2 is a schematic illustration of a beam of radiation impinging on a container, illustrated as an opaque container, with the walls of the opaque container shown transparently, illustrating example paths of radiation within the container.

With reference to FIG. 2, a beam of radiation 208 directed at a generally opaque container 204 containing a sample 202 is illustrated. While in the illustrated embodiment the container 204 is generally opaque, the walls of the container are shown transparently for illustrative purposes so that the movement of radiation 212 from the beam of radiation 208 that passes through the container 204 and into the sample may be easily seen. Generally, a portion of the beam of radiation 208 does not pass through and/or is reflected from the opaque container 204. Another portion of the radiation 212 passes through the container 204. For example, in one embodiment, approximately 1% of the radiation from the beam of radiation 208 passes through the generally opaque container. The portion of the radiation 212 that passes through the container 204 is scattered by the sample 202 and passes through the sample 202 in various directions. At least some of the radiation 212 is also reflected proximate the interface between the sample 202 and the container 204. Thus, having been reflected, the radiation 212 will again travel through the sample 202 by a path different than its original path, and then may again be reflected proximate the interface between the sample 202 and the container 204. Thus, portions of radiation make multiples passes with multiple different paths through different locations in the sample 202. The radiation 212 tends to encounter molecules of the sample in various different locations in the sample. Radiation 212 scatters throughout the sample, e.g., portions of the sample that do not absorb or block the radiation. The radiation 212 may be diffusely scattered, e.g., randomly.

Figure 3:
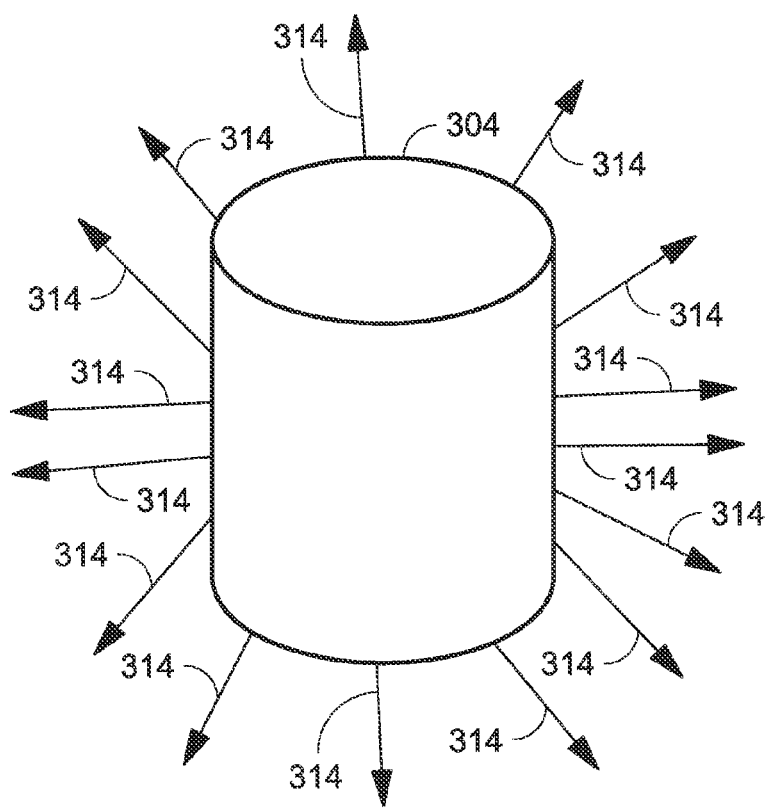
FIG. 3 is a schematic illustration of Raman radiation being emitted from the opaque container of FIG. 2.

With reference to FIGS. 2 and 3, the molecules of the sample 202 in different locations encountering the radiation emit Raman radiation 314 in various different directions, at least a portion of which Raman radiation 314 passes through the container 304. A transmission Raman signal includes a combination of this Raman radiation from the various different molecules at different locations in the sample, e.g., a "bulk" signal, indicative of the substances contained in the sample at various locations. In one embodiment, Raman analysis does not rely on absorption of the radiation 212, and a transmission Raman signal may be representative of the entire sample, such as not limited to the container material, coatings, outer portions of samples surrounding inner portions of samples, or the like.

With further reference to FIG. 1, in one embodiment, the detector 110 is configured to detect the transmission Raman signal, e.g., the "bulk" signal, combination of Raman signals emitted from different locations and/or different molecules in the sample 102, etc. The transmission Raman signal is emitted in various directions from the opaque container 304 (see FIG. 3), and detection of the transmission Raman signal from the sample in the opaque container has a low angular dependency or low variation based on detection angle. In the embodiment illustrated in FIG. 1, the beam of radiation 108 is directed at a first location 116 on the container 104, while the detector 110 is directed at a second location 118. Unlike other systems, because the detector 110 does not require receiving back-scattered radiation from the beam of radiation 108, the first location 116 and the second location 118 need not be the same. In the illustrated embodiment, the first location 116 is an angular distance θ from the second location 118.

In one embodiment, the portion of the container through which the radiation passes is between approximately 0.004 inches and 0.12 inches in thickness. In one embodiment, the laser 106 has a power of between approximately 50 mW and approximately 500 mW. In embodiments of the system 100, the power of the laser 106 is sufficient and the detector 110 is sufficiently sensitive to detect a transmission Raman signal from a sample contained in a generally opaque container, such as a container where the portion of the container through which the radiation passes is between approximately 0.004 inches and 0.12 inches in thickness.

In one embodiment, when the container 104 is generally opaque, the transmission Raman signal is indicative of the sample itself and is not overwhelmed by the background signal from the container material 104. For example, the transmission Raman signal is indicative of the sample 102, and not appreciably obscured by a signal indicative of the type of material from which the container is formed regardless of the magnitude of non-zero angular distance θ between the first location 116 and the second location 118.

In one embodiment, the system 100 is further configured to analyze samples in generally transparent containers. When the beam of radiation 108 reaches the generally transparent container, a larger portion of the radiation of the beam passes through the container 104 and into the sample 102 than when the container is generally opaque. Here, the radiation in the sample 102 may tend to reflect within the sample 102 proximate the interface between the sample 102 and the container 104 generally less than when the container 104 is generally opaque, meaning that less of the sample 102 will encounter radiation from the beam of radiation 108. That is, the radiation may travel to fewer locations in the sample than, for example, in a generally opaque container in which the radiation may be reflected multiple times and pass throughout the sample. For example, the radiation may generally encounter the sample only generally along the path of the beam of radiation in containers without substantial internal reflection. However, Raman radiation is emitted by some molecules in the sample 102 encountering the radiation. The combination of Raman radiation from different locations in the sample provides a transmission Raman signal of the sample in the transparent container.

In one embodiment, when the container 104 containing the sample 102 is generally transparent, the intensity of the transmission Raman signal may be angularly dependent. In one embodiment, the detector 110 may sense the greatest intensity Raman signal from a sample 102 in a generally transparent container 104 when the angular distance θ between the first location 116 and the second location 118, e.g., angular distance between location on the container 104 to which the laser 106 is directed and the location on the container to which the detector 110 is directed, is approximately 135°. In one embodiment, the detector 110 may sense local maximum intensities of the Raman signal from a sample 102 in a generally transparent container when the angular distance θ between the first location 116 and the second location 118 is approximately 45° or when the angular distance θ between the first location 116 and the second location is approximately 90°.

In one embodiment, when the container 104 containing the sample 102 is generally transparent, when the angular distance θ between the first location 116 and the second location 118 is approximately 180°, the signal detected by the detector 110 is indicative of the material of the container, such as where the background signal of the bottle material is greater so the signal emitted by the sample is generally undetectable at the outer radiation entry point on the container 104.

With further reference to FIG. 1, in one embodiment, the system 100 also includes a processor 120. The processor 120 is coupled to the laser 106 and to the image detector 110. The processor 120 is configured to receive information regarding the transmission Raman signal from the detector 110 and to utilize this information to analyze the sample 102.

Figure 4:
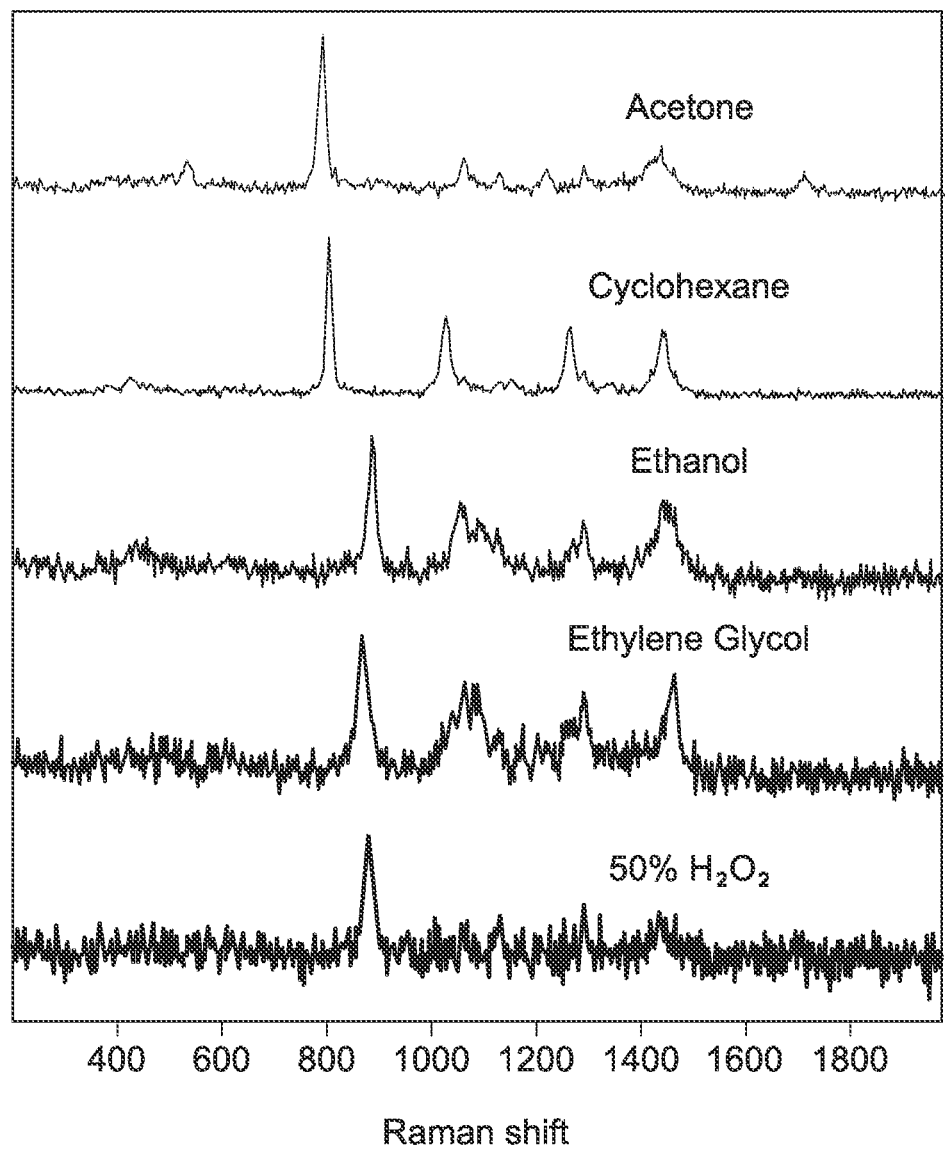
FIG. 4 is a graph showing Raman spectra indicative of exemplary substances of interest contained in generally opaque containers, plotted on axes of Raman shift vs. Raman intensity.

With reference to FIGS. 1 and 4, in one embodiment, the processor 120 is configured to compare characteristics of the transmission Raman signal, e.g., wavelength, etc., with characteristics of the beam of radiation 108 to analyze the sample 102. FIG. 4 illustrates a graph showing the Raman spectra of various exemplary substances that may be of interest contained in a generally opaque container. For example, the energy difference between the transmission Raman signal and the beam of radiation 108 may be compared to determine the Raman spectrum, e.g., fingerprint, of the sample. In the embodiment illustrated in FIG. 4, the x-axis is the Raman shift, in the illustrated embodiment in units of wavenumber. In one embodiment, this may be determined by subtracting the wavelength of the beam of radiation 108 from the wavelength of the transmission Raman signal. In one embodiment, the y-axis is the intensity. In one embodiment, the intensity may be determined from the detector based on the transmission Raman signal received.

In one embodiment, the processor 120 includes a library of signal characteristics indicative of substances in samples that may be of interest (e.g., dangerous substances, illicit substances, impurities, etc.). The processor 120 is configured to compare the characteristics of the transmission Raman signal received by the detector 110 with information in the library of signal characteristics to determine whether a sample contains substances of interest. In one embodiment, the processor 120 is configured to output to a user an indication of whether or not a sample contains one of the predetermined substances with characteristics stored in the library, e.g., visual output, audio output, electric signal output, etc.

With further reference to FIG. 1, in one embodiment, the system 100 includes an additional sensor 122. This additional sensor 122 is configured to indicate when a container 104 is located relative to the system 100 such that a sample 102 contained in the container 104 may be analyzed by the system 100. In one embodiment, the additional sensor 122 is coupled to the laser 106. In another embodiment, the additional sensor 122 is coupled to the processor 120. In one embodiment, the sensor 122 is pressure sensor configured to output a signal when a container 104 is properly located relative to the system 100. In another embodiment, the sensor 122 is an optical sensor configured to detect when a container 104 is properly located relative to the system 100. In other embodiments, other suitable sensors may be used.

In one embodiment, existing analysis devices, such as, e.g., a RespondeR BLS™, commercially available from Smiths Detection®, etc., may be retrofit to perform embodiments of methods described above.

In one embodiment, the container 104 is formed from plastic. In another embodiment, the container 104 is formed from glass. The laser 106 is configured to emit a beam of radiation such that sufficient radiation passes through the container 104 and into the sample 102 so that the sample 102 will emit a transmission Raman signal sufficient to be detected by the detector 110. In one embodiment, the laser 106 has a power of between approximately 50 milliwatts (mW) and approximately 500 mW. In one embodiment, the sidewall of the container 104 is between approximately 0.1 mm and approximately 3 mm thick. In one embodiment, samples contained in containers formed from HDPE may be analyzed by embodiments of systems 100 described above.

In various embodiments, systems 100 described above configured to analyze samples in containers may provide the ability to analyze samples in opaque containers without removing the samples from the containers. In some embodiments, the system 100 may be configured to minimize the background signal from the material of the container itself to allow analysis of the sample within the container. In some embodiments, relative insensitivity to optical alignment of the radiation source and the detector may allow for high throughput (e.g., large volume of samples analyzed in short period of time, etc.), reliable detection of substances of interest within samples, and a low rate of false alarm (e.g., low number of occurrences of indication from processor of substance of interest being present in a sample when in fact no substance of interest is present in the sample, low number of occurrences of indication from processor of substance of interest not being present in sample when in fact substance of interest is present in the sample, etc.).

In other embodiment, multiple energy sources located at multiple locations and directing light at multiple locations on a container containing a sample may be provided. In one embodiment, this configuration with multiple energy sources may improve signal collection efficiency.

In another exemplary embodiment implementation using ubiquitous transmission Raman spectroscopy, such as with the transmission Raman sample analysis system 100, a radiation beam from laser 106, which may emit focused or non-focused probe light, is directed through the wall or bottom of container 104. The laser beam becomes a diffusive light source within the container 104 with no formation of a distinct sample region. In this implementation, a whole liquid sample 102 is illuminated by the internal reflection of lasers between the inner walls of the container 104. A Raman signal is generated from multi-path laser excitation of the whole liquid sample 102 within the container 104. The ubiquitous Raman signal can be transmitted and received in omni-direction. Advantages of using transmission Raman spectroscopy can include a transparent, sufficiently transparent, and/or opaque delivery region (e.g., bottle material or the like). Additionally, the sample region can include the whole liquid sample 102. The collection optics (e.g., detector 110) can include focus and/or non-focus optics, and the laser light beam within the sample 102 can function as a diffusive light source. The whole liquid sample 102 can be illuminated due to the internal reflection of the laser beams. The Raman signal source can be from multi-path laser excitation instead of only from a single laser beam path. Using non-focus optics can prevent burning on dark-colored materials (e.g., plastic bottles, labels, or the like). Further, the Raman signal collection can be from the whole container 104 because of the omnidirectional collection, and the delivery region and the collection path can be non-concentric as well as concentric.

In one embodiment, a system 100 may be configured to analyze containers containing multiple samples, e.g., multi-container.

In one embodiment, a system 100 may be configured to determine the composition of a container and to determine the composition of a sample in the container, e.g., another detector may be directed at a location on a container, e.g., approximately 180° from a location on a container to which a energy source is directed, etc., and configured to detect a signal from the container material itself.

In an exemplary embodiment, no reference beam is used, and container or bottle background is recognized, and removed if substantial. Here, a single collection path may be used to collect the Raman signal. If the container background component is found to be relatively strong, other means to remove it are used, such as a characteristic lookup table for particular materials. The characteristic lookup table may include predicted Raman signals for various types of glass and/or plastic.

Embodiments of processors 120 may include analog-to-digital converters, digital-to-analog converters, amplification elements, microprocessors, etc., as will be further explained below. Processors are not limited by the materials from which they are formed or the processing mechanisms employed therein. For example, the processor may be comprised of semiconductor(s) and/or transistors (e.g., electronic integrated circuits (ICs)). Memory can be included with the processor. Memory can store data, such as algorithms configured to compare. Although a single memory device can be used, a wide variety of types and combinations of memory (e.g., tangible memory) may be employed, such as random access memory (RAM), hard disk memory, removable medium memory, external memory, and other types of computer-readable storage media.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In additional embodiments, a variety of analytical devices may make use of the structures, techniques, approaches, and so on described herein. A variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

In embodiments, the system, including its components, operates under computer control. For example, a processor included with or in the system to control components and functions described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the system. In the case of a software implementation, the module, functionality, or logic represents program code that performs specified tasks when executed on a processor (e.g., CPU or CPUs). The program code may be stored in one or more computer-readable memory devices (e.g., memory and/or one or more tangible media), and so on. The structures, functions, approaches, and techniques described in this document can be implemented on a variety of computing platforms having a variety of processors.

Memory can be included with the processor. The memory can store data, such as a program of instructions for operating the system (including its components), data, and so on. Although a single memory device can be used, a wide variety of types and combinations of memory (e.g., tangible memory, non-transitory) may be employed, such as random access memory (RAM), hard disk memory, removable medium memory, external memory, and other types of computer-readable storage media.

Although this disclosure has described embodiments in a structural manner, the structure and its structural and/or functional equivalents can perform methods.

Variations of the embodiments disclosed in this document will be apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:

1. A system configured to analyze a sample in a container, the system comprising:
   an emitter configured to emit radiation directed at a first location on the container, at least a portion of the radiation passing through the container and into the sample, with at least a portion of the radiation in the sample being reflected within the container to make multiple passes wherein each of the multiple passes follows a different path through the sample to provide a plurality of different locations in the sample; and
   a detector with a receiving portion directed at a second location on the container, the detector being configured to receive a transmission Raman signal including Raman radiation from multiple portions at the plurality of different locations in the sample,
   wherein an intensity of the transmission Raman signal is angularly independent if the beam of radiation is directed at a generally opaque container.

2. The system of claim 1, wherein the first location is an angular distance of between approximately 1° and approximately 179° from the second location.

3. The system of claim 1, wherein the first location is an angular distance of one of approximately 135°, approximately 45°, and approximately 90° from the second location.

4. The system of claim 1, wherein the first location is not located an angular distance of approximately 180° from the second location.

5. The system of claim 1, wherein the system is configured to analyze samples within containers both generally opaque to visible light and containers generally transparent to visible light.

6. The system of claim 1, further comprising a sensor configured to determine when a container is configured relative to the system such that a sample within the container may be analyzed by the system.

7. The system of claim 6, wherein the sensor is a pressure sensor configured to sense the presence of a container.

8. The system of claim 1, further comprising a second detector directed at a third location on the container located approximately 180° from one of the first or second locations, the second detector configured to receive a signal including Raman radiation indicative of the material of the container.

9. The system of claim 1, further comprising a processor configured to indicate the presence of predetermined substances within the sample based on the output of the comparator.

10. The system of claim 1, further comprising a comparator configured to compare at least one of the intensity, wavelength, direction of propagation, beam size or waveform of the transmission Raman signal with the radiation emitted by the emitter.

11. The system of claim 1, wherein the angular distance between the entry point through a wall of the container of the emission path and the entry point through a wall of the container of the detection path is greater than zero degrees and less than 180 degrees.

12. A method of transmission Raman analysis comprising:
   emitting radiation towards a first wall portion of a container, wherein the emitted radiation becomes a diffusive light source within the container without formation of a distinct sample region; and
   receiving a transmission Raman signal through a second wall portion of the container, the received signal including Raman radiation reflected from multiple portions of the container,
   wherein an intensity of the transmission Raman signal is angularly independent if the radiation is directed at a generally opaque container.

13. The method of claim 12, further comprising comparing the transmission Raman signal with the emitted radiation.

14. The method of claim 12, wherein the Raman signal is received through a collection path that is not focused on any distinct sample region within the container.

15. The method of claim 12, wherein no reference beam is used, the method further comprising:
   receiving a Raman signal including container background information;
   looking up matching container background information; and
   subtracting the looked-up container background information from the received Raman signal.

16. The method of claim 15, wherein the matching container background information is selected from a table comprising entries for a plurality of glass types and a plurality of plastic types.

17. The method of claim 12, wherein the emitted radiation follows an incident non-reflected path that intersects a collection path of the Raman radiation corresponding to the received Raman signal.

18. The method of claim 12, wherein at least one of the emitted radiation or Raman radiation illuminates the entire contents of the container by the internal reflection of radiation between the inner walls of the container.

19. The method of claim 12, wherein a Raman signal is generated from multi-path excitation of a whole liquid sample within the container.

20. The method of claim 12, wherein the Raman signal is at least one of omni-directional or ubiquitous.

21. The method of claim 12, wherein the container is generally opaque to visible light.

22. The method of claim 12, wherein said first wall portion is defined by an outer surface of the container, and said second wall portion is defined by an inner surface of the container directly interior to said outer surface.

23. A method of analyzing a sample in a container having an interior surface and an exterior surface, the method comprising:
   directing a beam of radiation at the container such that at least a portion of the radiation passes through the container and is scattered in the sample and at least a portion of the scattered radiation reflects off of the interior surface of the container, the radiation in the sample resulting in emission of a Raman signal representative of the contents of the sample at a plurality of locations within the sample;
   detecting the Raman signal representative of the contents of the sample at a plurality of locations within the sample; and
   comparing the Raman signal to the radiation of the radiation source,
   wherein an intensity of the Raman signal is angularly independent if the beam of radiation is directed at a generally opaque container.

24. The method of claim 23, further comprising:
   wherein the directing comprises at least one of:
   directing a beam of radiation at a container generally opaque to visible light and detecting the Raman signal representative of the contents of a sample contained in the generally opaque container; or directing a beam of radiation at a non-opaque container and detecting the Raman signal representative of the contents of a sample contained in the non-opaque container.

25. The method of claim 23, wherein the radiation source is a laser of between approximately 50 mW and 500 mW.

26. The method of claim 23, wherein the sample comprises a liquid sample.

27. The method of claim 23, wherein the radiation source is configured to emit a beam of radiation sufficient that a sample contained in a generally opaque container will emit a transmission Raman signal sufficient for the detecting.

28. The method of claim 23, wherein the radiation in the sample is reflected in the container; and wherein the radiation travels in the sample resulting in emission of Raman radiation at various angular orientations with respect to each other, respectively.

29. A method of analyzing liquid samples in both generally opaque to visible light containers and generally transparent containers, respectively, comprising:

directing a beam of radiation at a first location on a container containing a liquid sample;

directing a detector at a second location on the container, the second location being different from the first location;

wherein the beam of radiation and the detector are configured so a sufficient amount of radiation from the beam passes through the container and into the sample to produce a sufficient transmission Raman signal including Raman radiation from a plurality of locations in the sample so the detector can detect the transmission Raman signal, the transmission Raman signal being indicative of the composition of the sample;

comparing the transmission Raman signal with the radiation emitted by the emitter;

determining based on a library of characteristics of substances of interest whether the transmission Raman signal indicates that the sample contains a substance of interest; and outputting whether or not the sample contains a substance of interest, wherein an intensity of the transmission Raman signal is angularly independent if the beam of radiation is directed at a generally opaque container.

30. The method of claim 29, further comprising determining whether the transmission Raman signal indicates that the sample contains at least one of acetone, cyclohexane, ethanol, ethylene glycol, or $H_2O_2$ and outputting a warning if it is determined that the transmission Raman signal indicates that the sample contains at least one of acetone, cyclohexane, ethanol, ethylene glycol, or $H_2O_2$.

31. The method of claim 29, wherein the first location is approximately 135° from the second location.

32. The method of claim 29, further comprising before directing the beam of radiation at the first location on the container, detecting whether a container is located to receive the beam of radiation.

* * * * *